(12) United States Patent
Pearlman et al.

(10) Patent No.: US 8,852,899 B2
(45) Date of Patent: Oct. 7, 2014

(54) METHODS OF MAKING NYLON INTERMEDIATES FROM GLYCEROL

(75) Inventors: Paul S. Pearlman, Thornton, PA (US); Changlin Chen, Ingleby Barwick (GB); Adriana L. Botes, Rosedale East (GB)

(73) Assignee: INVISTA North America S.a.r.l., Wilmington, DE (US)

( * ) Notice: Subject to any disclaimer, the term of this patent is extended or adjusted under 35 U.S.C. 154(b) by 0 days.

(21) Appl. No.: 13/524,883

(22) Filed: Jun. 15, 2012

(65) Prior Publication Data

US 2013/0210090 A1  Aug. 15, 2013

Related U.S. Application Data

(60) Provisional application No. 61/498,396, filed on Jun. 17, 2011.

(51) Int. Cl.

| | | |
|---|---|---|
| C12P 21/02 | (2006.01) | |
| C12P 7/16 | (2006.01) | |
| C12P 7/28 | (2006.01) | |
| C12P 17/12 | (2006.01) | |
| C12P 17/10 | (2006.01) | |
| C12P 1/04 | (2006.01) | |
| C12R 1/01 | (2006.01) | |
| A61K 35/74 | (2006.01) | |
| A61K 38/00 | (2006.01) | |
| C12N 1/32 | (2006.01) | |
| C07K 14/195 | (2006.01) | |
| C12N 9/78 | (2006.01) | |
| C12N 9/10 | (2006.01) | |
| C12P 13/02 | (2006.01) | |
| C12P 13/00 | (2006.01) | |
| C12N 15/52 | (2006.01) | |
| C12P 7/04 | (2006.01) | |
| C12N 9/02 | (2006.01) | |
| C12N 9/88 | (2006.01) | |
| C12P 5/02 | (2006.01) | |
| C12N 9/04 | (2006.01) | |
| C12P 7/18 | (2006.01) | |
| C12P 7/42 | (2006.01) | |
| C12P 7/46 | (2006.01) | |
| C07K 14/37 | (2006.01) | |

(52) U.S. Cl.
CPC ... *C12P 7/42* (2013.01); *C12N 1/32* (2013.01); *C12Y 203/01009* (2013.01); *C07K 14/195* (2013.01); *C12N 9/78* (2013.01); *C12Y 401/01005* (2013.01); *C12N 9/1029* (2013.01); *C12P 13/02* (2013.01); *C12P 13/001* (2013.01); *C12Y 202/01006* (2013.01); *C12N 9/1096* (2013.01); *C12N 15/52* (2013.01); *C12Y 101/01157* (2013.01); *C12N 9/1022* (2013.01); *C12P 13/005* (2013.01); *C12P 7/04* (2013.01); *C12N 9/0008* (2013.01); *C12N 9/88* (2013.01); *C12P 5/02* (2013.01); *C12P 5/026* (2013.01); *C12N 9/0006* (2013.01); *C12P 7/18* (2013.01); *C12P 7/46* (2013.01); *C07K 14/37* (2013.01); *C12Y 101/01004* (2013.01)

USPC ........... 435/121; 435/71.2; 435/170; 435/160

(58) Field of Classification Search
None
See application file for complete search history.

(56) References Cited

U.S. PATENT DOCUMENTS 6,372,939 B1 * 4/2002 Bunel et al. .................. 562/553
8,088,607 B2 * 1/2012 Burgard et al. ............... 435/128

FOREIGN PATENT DOCUMENTS

| WO | WO 2008/006037 | 1/2008 |
|---|---|---|
| WO | WO 2011/003034 | 1/2011 |

OTHER PUBLICATIONS

Paulo da Silva et al. "Glycerol: A promising and abundant carbon source for industrial microbiology" 2009 Biotechnology Advances 27 30-39.*
International Search Report and Written Opinion in International Application No. PCT/US2012/042747, mailed Jan. 14, 2013, 19 pages.
Jung et al., "Production of 1,2-Propanediol from Glycerol in *Saccharomyces cerevisiae*," *J. Microbiology and Biotechnology*, May 19, 2011, 21(8):846-853.
Ferreira et al. "A member of the sugar transporter family, Stl1p is the glycerol/H= symporter in *Saccharomyces cerevisiae*," *Molecular Biology of the Cell, American Society for Cell Biology*, Apr. 1, 2005, 16(4):2068-2076.
Nicol et al., "Bioconversion of crude glycerol by fungi," *Applied Microbiology and Biotechnology*, Feb. 10, 2012, 93(5):1865-1875.

* cited by examiner

*Primary Examiner* — Suzanne M Noakes
*Assistant Examiner* — Gerard Lacourciere
(74) *Attorney, Agent, or Firm* — Fish & Richardson P.C.

(57) ABSTRACT

Embodiments of the invention relate to the enzymatic conversion of bioderived feedstocks to commercially valuable chemicals. The enzymatic conversions of the embodiments of the invention offer the potential for lower cost routes to these value-added chemicals. Some of the chemicals that are useful include nylon intermediates such as caprolactam, adipic acid, 1,6-hexamethylene diamine; butanediols such as 1,4-butanediol, 1,3-butanediol, and 2,3-butanediol; butanols such as 1-butanol, and 2-butanol; succinic acid, butadiene, isoprene, and 3-hydroxypropanoic acid.

13 Claims, 3 Drawing Sheets

METHODS OF MAKING NYLON INTERMEDIATES FROM GLYCEROL

CROSS-REFERENCE TO RELATED APPLICATIONS

This application claims the benefit of U.S. Provisional Appl. Ser. No. 61/498,396, filed Jun. 17, 2011, which is incorporated by reference as if fully set forth herein.

FIELD OF THE INVENTION

This application is related to methods of improving the conversion of glycerol into chemicals or intermediates and host cells which are capable of performing these conversions.

BACKGROUND OF THE INVENTION

Microbial conversion of bioderived feedstocks to commercially valuable chemicals offers the potential for lower cost routes to these products. Some of the chemicals that are useful include nylon intermediates such as caprolactam, adipic acid, 1,6-hexamethylene diamine; butanediols such as 1,4-butanediol, 1,3-butanediol, and 2,3-butanediol; butanols such as 1-butanol, and 2-butanol; succinic acid, butadiene, isoprene, and 3-hydroxypropanoic acid.

Most microbial processes rely on carbohydrates (such as sucrose or glucose) as the preferred feedstock. It is more advantageous to utilise alternative lower cost feedstocks such as glycerol, syngas or fatty acids. Glycerol is a by-product of biodiesel production and it can be a low cost feedstock as the production of biodiesel increases. In microbial processes utilizing glycerol as a feedstock, a natural organism such as a bacterium, *Escherichia coli*, or *Clostridium* sp and the like or a fungus, *Candida* sp, or *Yarrowia lipolytica*, or *Aspergillus* sp with a natural ability to metabolise glycerol is genetically modified to incorporate the required pathway to desired product.

Utilizing a host organism that naturally metabolise glycerol limits the ability to optimize the overall commercial efficiency of the production of the desired products as these host organisms may not be ideal hosts for the defined pathway to produce the product.

Accordingly, against this background, it is clear that there is a need for a method to produce chemicals or intermediates utilizing an organism which is genetically modified to impart or improve its metabolism of glycerol and its ability to produce a desired product through a metabolic pathway from glycerol.

SUMMARY OF THE INVENTION

Against this background, the inventors have identified means for improving the conversion of glycerol, a potentially low cost, renewable feedstock, into a number of chemicals including those which have use in the synthesis of nylons, using whole cell biocatalysts.

It is the inventors' discovery that a microorganism strain could be generated that is genetically modified by expression of an active glycerol protein transporter, the glycerol facilitator (also known as the major intrinsic protein MIP). Said strain is further optionally able to grow on glycerol as the sole carbon and energy source and contains a non-naturally occurring metabolic pathway to convert glycerol to the desired product.

In some embodiments, the naturally occurring glycerol protein transporter is constructed in a host organism with a different or modified glycerol protein transporter and the resultant engineered organism has improved ability to efficiently transport and metabolize glycerol as compared to the unmodified organism.

In some embodiments, the naturally occurring glycerol protein transporter is constructed in a host microorganism with a different or modified glycerol protein transporter and the resultant engineered organism is able to tolerate higher glycerol loadings.

In some embodiments, an active glycerol protein transporter is introduced into a microorganism that does not naturally metabolise glycerol and the resultant engineered organism is able to metabolise glycerol effectively.

In some embodiments, the desired product produced from the modified organism is a nylon intermediate selected from hexane-1,6-dioic acid, hexane-1,6-diamine (hexamethylenediamine), 6-aminohexanoic acid, and caprolactam.

In some embodiments, the desired product produced from the modified organism is a $\alpha,\omega$-difunctional amine, dicarboxylic acid, aminoacid, or lactam.

In some embodiments, the desired product produced from the modified organism is a hydroxylated alkane selected from the butanediol such as 1,4-butanediol, 1,3-butanediol, and 2,3-butanediol; propanediol such as 1,3-propanediol and 1,2-propanediol; and butanol such as 1-butanol and 2-butanol.

In some embodiments, the desired product produced from the modified organism is butadiene.

In some embodiments, the glycerol that is used as a substrate in the method has been produced as the by-product of bio-diesel production.

In some embodiments, the glycerol that is used as a substrate in the method is a crude glycerol containing at least 15% water and has been produced as the by-product of bio-diesel production.

In some embodiments, the host cell of the invention is able to utilise glycerol as the sole carbon source for growth.

Advantageously, by use of the method of the present invention, the use of petrochemical-based raw materials is reduced and a sustainable process, which can use the waste products from a commercial industrial process (i.e. biodiesel production), is provided. Furthermore, the process can be operated in existing plants without requiring new chemical or fermentation plants to be built. As the feedstock can be generated in situ, transport costs and rates are minimised.

DETAILED DESCRIPTION OF THE INVENTION

The method of the invention uses a whole cell organism which has been genetically modified to improve the uptake of glycerol and the conversion of glycerol to a desired product.

Another invention uses a microorganism to convert glycerol to a desired product wherein the microorganism has been genetically modified to introduce or improve its ability to metabolise glycerol.

Suitable techniques for identifying, isolating and modifying target enzymes through DNA recombination are known in the art.

1.1. Enzyme Catalysed Conversions

The methods of the present invention provide the means to convert glycerol into a range of intermediates which have use in the synthesis of nylons.

The core of the invention is the use of enzymes to divert metabolites produced in cells in the central pathways of metabolism (i.e. glycolysis and the TCA cycle) into the desired intermediates useful in the manufacture of nylon.

1.1.1. Glycerol Uptake

Central to the invention is an organism's ability to take in glycerol from its surroundings so that it can be transformed in the reaction pathways described above. The ability and efficiency of microorganisms to utilise glycerol is related to the organism's capacity of assimilation (uptake) of glycerol, and its ability to convert it into either microbial biomass or chemical end products secreted out of the cell. Of course, the ability to convert it into either microbial biomass or chemical end products secreted out of the cell means nothing unless the glycerol has been assimilated in the first place.

The present invention solves this problem by using cells which have been engineered, whether it is a known glycerol-utilising organism or not, with an active glycerol protein transporter, the glycerol facilitator on the host organism cell membrane. The glycerol facilitators include the glycerol MIP family channels (i.e., GipF) from bacteria, such as *Escherichia coli, Bacillus subtilis, Streptomyces coelicolor, Clostridium* spp, *Methanobacterium* spp, and the like, the tonoplast intrinsic proteins (TIPs, and/or aquaporins) from algae or plants, such as *Ostreococcus lucimarinus, Chlamydomonas reinhardtii, Volvox carteri, Chlorella variabilis, Physcomitrella patens, Arabidopsis thaliana, Ricinus communis, Vitis vinifera, Populus trichocarpa*, the fungi and yeast glycerol channel proteins (Fps1), such as those from *Saccharomyces cerevisiae, Candida* spp, *Kluyveromyces* spp., *Yarrowia lipolytica, Asperigillus* spp, *Penicillium* spp., *Laccaria bicolor, Phytophthora infestans*, and *Ajellomyces capsulatus*. These glycerol transporters allow the facilitated diffusion of glycerol into the cell, thus make the host available to glycerol for subsequent metabolism.

1.1.2 Feeding of Glycerol to the Central Metabolism

Figure 1:
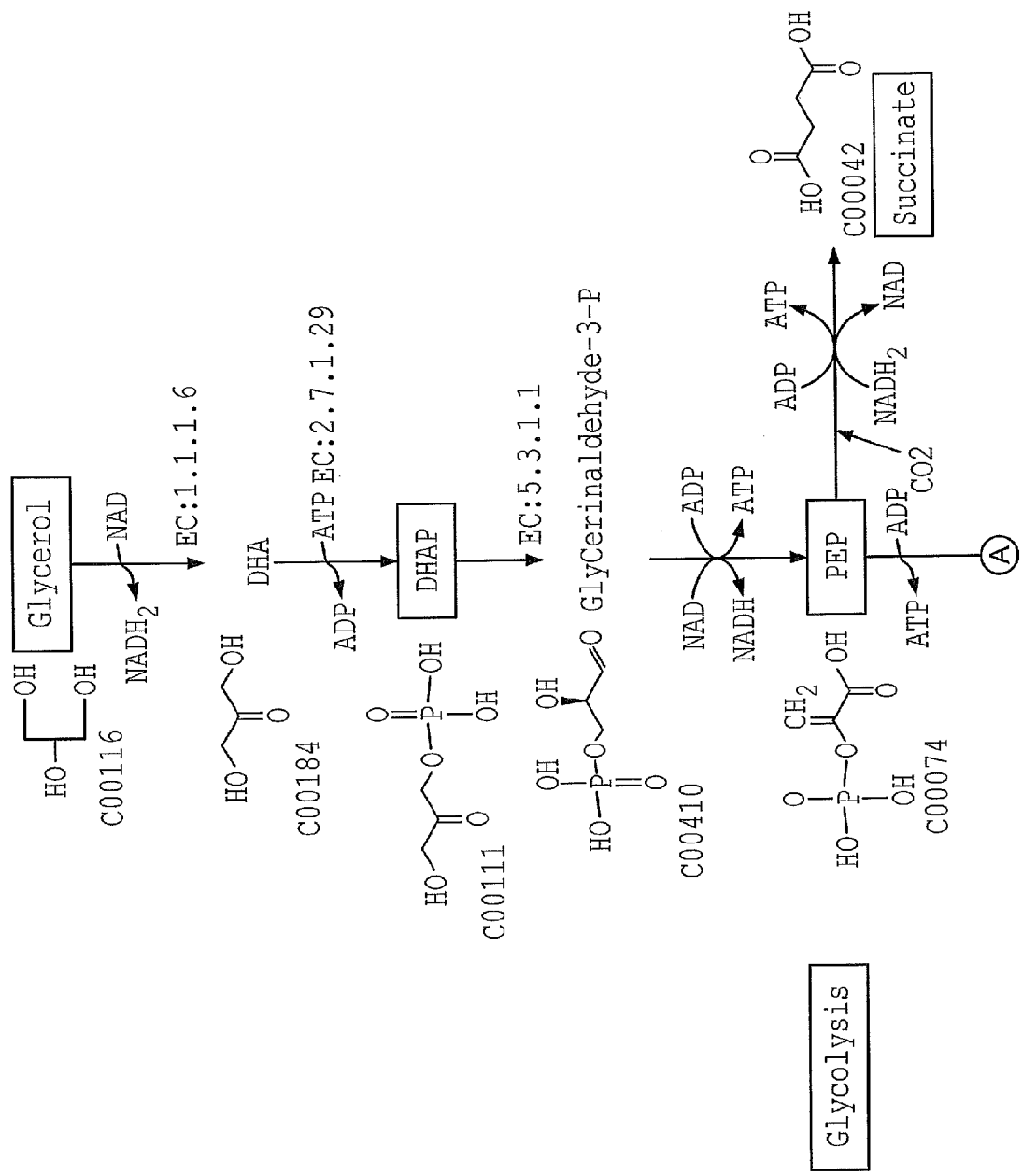
FIG. 1 is a schematic illustration of the enzyme catalysed reactions which convert glycerol into acetyl-CoA.
Figure 1:
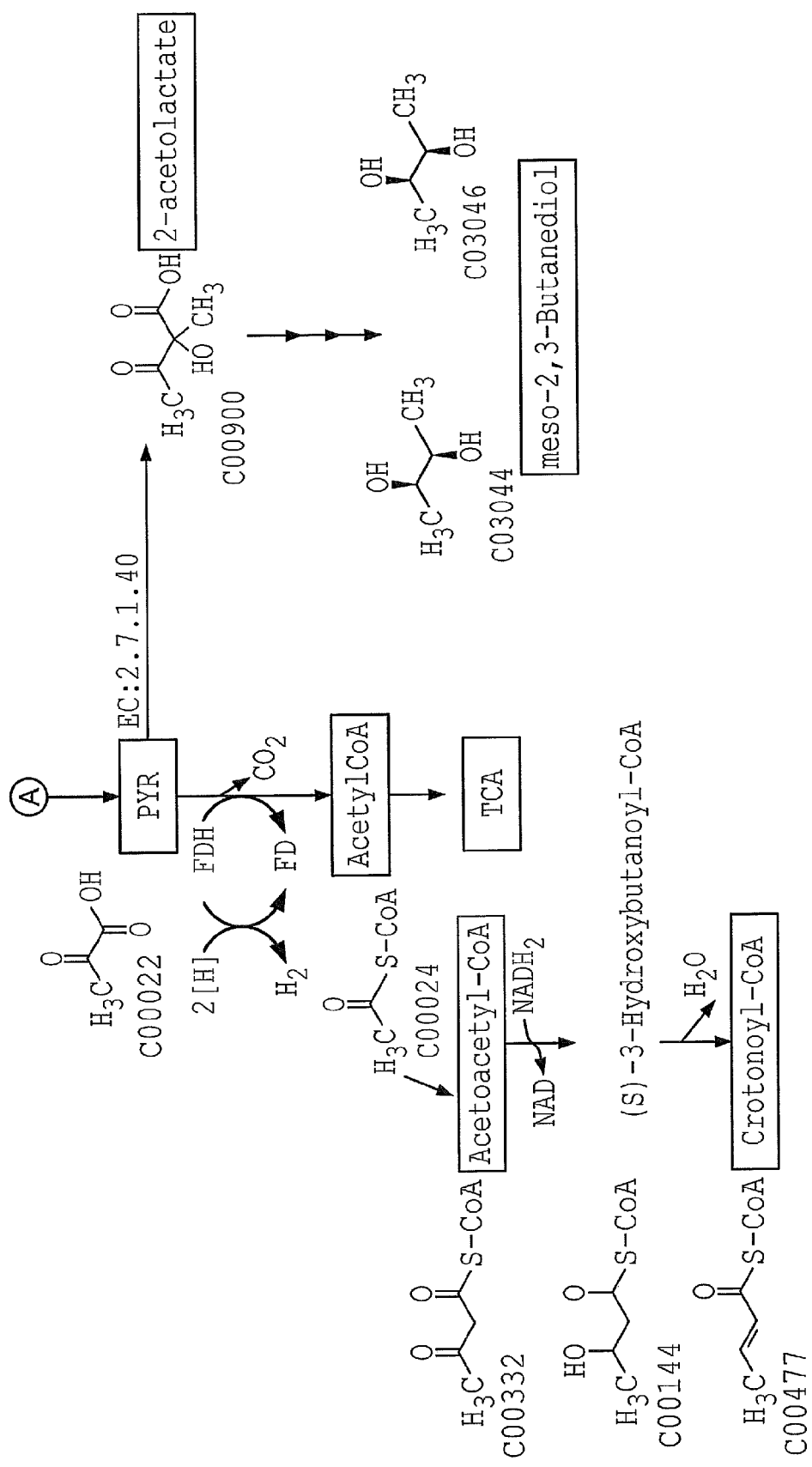
Figure 2A:
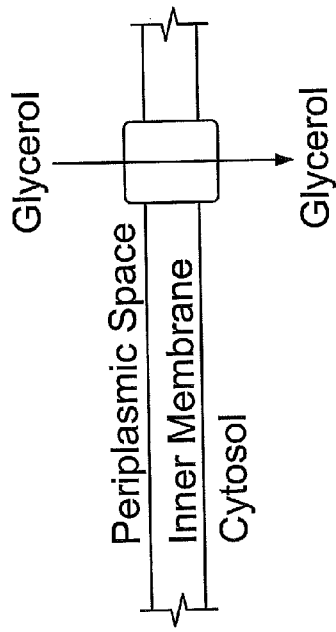
FIG. 2A a diagram showing the facilitated transport of glycerol.
Figure 2B:
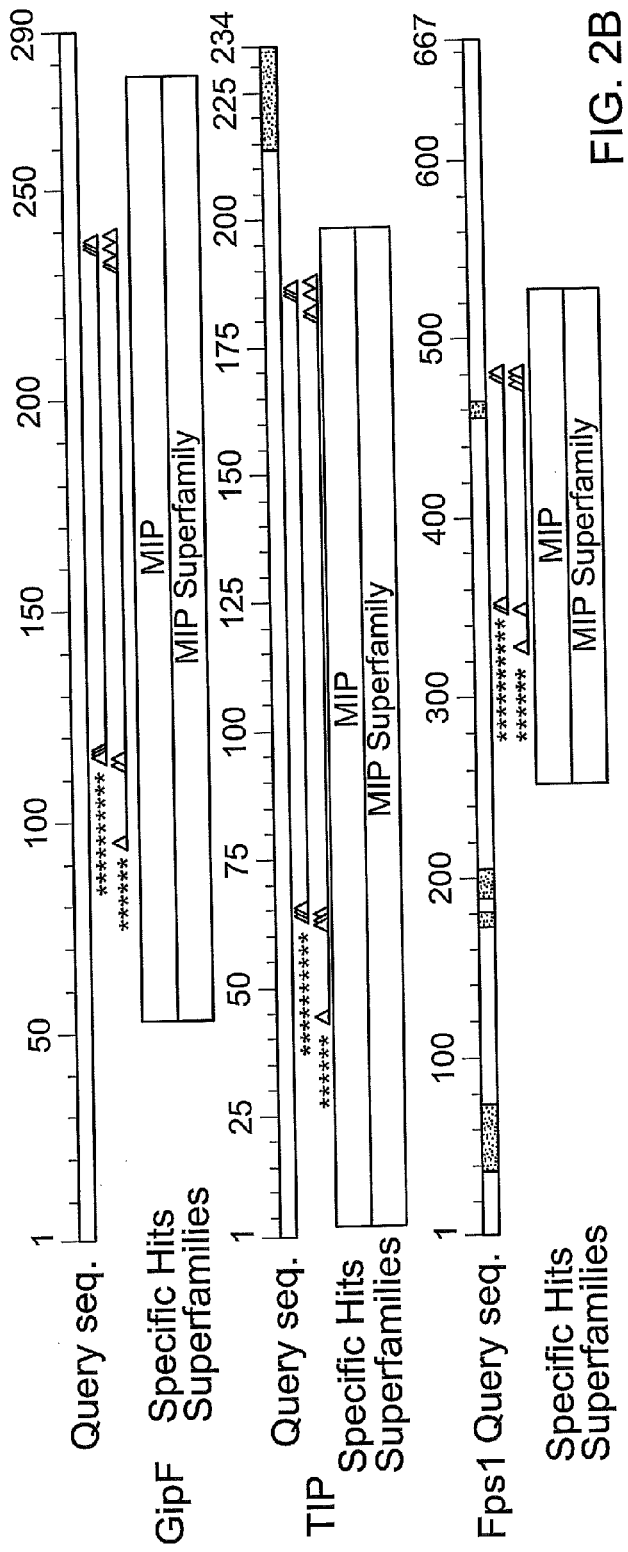
FIG. 2B a diagram showing the common domain structure of a number of glycerol transporter proteins.

The first series of reactions in the conversion of glycerol into intermediates which have use in the synthesis of chemicals is the feed in of glycerol into the central metabolism of the host cell performing the biocatalytic conversion. As illustrated in FIG. 1, first the glycerol is converted into dihydroxyacetone (DHA) by glycerol dehydrogenase. Following this step, DHA can undergo standard metabolic conversions to produce pyruvate, and from there acetyl-CoA and succinic acid. A review of the stepwise reactions leading from DHA to pyruvate, and enzymes suitable for performing these transformations, can be found in standard biochemical textbooks. Enzymes which perform these initial conversions may be identified and isolated by screening organisms for their ability to grow on glycerol as the sole carbon source. An ability to grow indicates that glycerol is being metabolised and thus is being transformed into metabolites which can feed into the central metabolism of the cell.

1.1.3. Production of 6-oxohexanoic Acid and Derivatives

It is possible to produce 6-oxohexanoic acid by diverting intermediates produced by the metabolic processes of glycolysis and the TCA cycle.

The central starting metabolite is acetyl-CoA, which is produced by the enzyme pathway detailed above. This metabolite may then be converted, through a series of reactions, into 6-oxohexanoic acid.

In order to produce derivatives of hexane-1,6-dioic acid, the hexane-1,6-dioic acid should first be converted into 6-oxohexanoic acid. This reaction can be achieved using an aldehyde dehydrogenase. Aldehyde dehydrogenase enzymes can be found in EC 1.2.1.4. Typical enzymes that are used include NADP-dependent aldehyde dehydrogenase enzymes, for example those from *Acetobacter rancens* CCM 1774, *Oryctolagus cuniculus, Saccharomyces cerevisiae, Gluconobacter melanogenus* or *Acinetobacter calcoaceticus*. Other suitable enzymes include 6-oxohexanoate dehydrogenases (ChnE), for example from *Acinetobacter* species (e.g. *Acinetobacter* NCIB 9871) and *Nocardia globerula*. Thus the invention provides a host cell comprising the enzymes for producing hexane-1,6-dioic acid from glycerol, as described above, and further comprising an aldehyde dehydrogenase, wherein the cell produces 6-oxohexanoic acid from glycerol.

6-Oxohexanoic acid can be converted into 6-aminohexanoic acid by the action of an aminotransferase. Suitable enzymes are found in EC 2.6.1. Typical enzymes that are used include those from *Pseudomonas putida* BS394, *Acinetobacter* spp., *Alcaligenes faecalis, Arthrobacter citreus, Arthrobacter* sp. KI72, *Lysinibacillus sphaericus, Paracoccus* sp, *Pseudomonas* spp., *Pseudomonas aeruginosa, Pseudomonas putida* KT2440, and *Rhodococcus rhodochrous*. Thus the invention provides a host organism comprising the enzymes for producing 6-oxohexanoic acid from glycerol, as described above, and further comprising an aminotransferase, wherein the cell produces 6-aminohexanoic acid from glycerol.

6-Aminohexanoic acid can be converted to caprolactam by the action of an amidohydrolase. Amidohydrolase enzymes catalyse the hydrolysis of amide linkages to generate a carboxylic acid group and an amine group. It has been demonstrated that these enzymes can also be forced to react in the reverse direction, catalysing the condensation of an amine and a carboxylic acid to form an amide bond. In the methods of the present invention, an amidohydrolase can be used in this reverse direction to catalyse the production of caprolactam from 6-aminohexanoic acid. Suitable enzymes are found in EC 3.5.2. Typical enzymes that are used include those from *Acromobacter guttatus* KI72, *Flavobacterium* spp. and *Pseudomonas* spp. Thus, in one embodiment the invention provides a host organism comprising the enzymes for producing 6-aminohexanoic acid from glycerol, as described above, and further comprising an amidohydrolase, wherein the cell produces caprolactam from glycerol.

6-Aminohexanoic acid can be converted to 6-aminohexanal by the action of an aldehyde dehydrogenase, as described above. Thus the invention provides a host cell comprising the enzymes for producing 6-aminohexanoic acid from glycerol, as described above, comprising an aldehyde dehydrogenase, wherein the cell produces 6-aminohexanal from glycerol.

6-Aminohexanal can be converted to hexane-1,6-diamine (hexamethylene diamine) by the action of an aminotransferase or a diamine transaminase (EC 2.6.1.29), as described above. Thus the invention provides a host cell comprising the enzymes for producing 6-aminohexanal acid from glycerol, as described above, comprising an aminotransferase, wherein the cell produces hexane-1,6-diamine from glycerol.

1.1.4. Production of Butadiene and Butanediols

As detailed in the preceding section, acetyl-CoA can be converted into 2-butenoyl-CoA (crotonoyl-CoA), as set out in FIG. 1.

First acetyl-CoA is converted into acetoacetyl-CoA (by acetyl-CoA C-acetyltransferase, EC 2.3.1.9). Acetoacetyl-CoA is then converted into (S)-3-hydroxybutanoyl-CoA (by 3-hydroxybutyryl-CoA dehydrogenase, EC 1.1.1.157). (S)-

3-hydroxybutanoyl-CoA is then converted into 2-butenoyl-CoA (crotonoyl-CoA) (by enoyl-CoA hydratase, EC 4.2.1.17).

As shown in FIG. 3, 2-butenoyl-CoA (crotonoyl-CoA) may then be converted into a range of molecules which are useful intermediates in the synthesis of nylons.

For example, 2-butenoyl-CoA (crotonoyl-CoA) can be converted into but-2-enoyl-CoA (vinylacetyl-CoA) (by vinylacetyl-CoA delta-isomerase, EC 5.3.3.3.). But-2-enoyl-CoA can then be converted into 4-hydroxybutyryl-CoA (by 4-hydroxybutanoyl-CoA dehydratase, EC 4.2.1.120). 4-hydroxybutyryl-CoA can then be converted into 4-hydroxybutanal (by a thiolester hydrolase, EC 3.1.2.-). 4-hydroxybutanal can then be converted into 1,4-butanediol (by an alcohol dehydrogenase, EC 1.1.1.202). In some embodiments, 1,4-butanediol is the desired intermediate, and no further reactions are performed. Thus in another embodiment, the invention provides a host cell comprising the enzymes as described herein and further comprising the enzymes set out above, wherein the host cell converts glycerol into butane-1,4-diol.

Alternatively, if 1,3-butadiene is the intended product, then 1,4-butanediol can be converted into 1,3-butadiene (by a hydrolyase, EC 4.2.1.-). Thus in another embodiment, the invention provides a host cell as described above for converting glycerol into butane-1,4-diol, further comprising an enzyme capable of converting 1,4-butanediol into 1,3-butadiene, wherein the host cell converts glycerol into 1,3-butadiene.

Another pathway for producing 1,3-butadiene is disclosed. It proceeds from 2-butenyl-CoA (crotonoyl-CoA) via 2-butenal (crotonic aldehyde) (e.g. catalysed by a reductase, EC 1.2.1.-) to 2-buten-1-ol (crotonic alcohol) (e.g. catalysed by a semialdehyde reductase EC 1.1.1.-) to 1,3-butadiene (e.g. catalysed by a hydrolyase, EC 4.2.1.-). Thus the invention provides a host cell comprising the enzymes described above for producing 2-butenyl-CoA, and further comprising enzymes capable of converting 2-butenyl-CoA into 2-butenal, 2-butenal into 2-buten-1-ol, and 2-buten-1-ol into 1,3-butadiene, wherein the host cell converts glycerol into glycerol into 1,3-butadiene.

A pathway for producing 1,3-butanediol from glycerol is also provided.

A pathway for producing 2,3-butanediol from glycerol, as illustrated in FIG. 1. Here, pyruvate is converted into 2-acetolactate and then into 2,3-butanediol.

1.1.5. Non-Naturally Occurring Enzymes and Proteins

In some embodiments, the enzymes used to perform conversions in the method of the invention are non-naturally occurring. That is to say the DNA encoding them has been mutated from the wild-type sequence in order to improve one or more of the enzyme's properties. Methods for mutagenesis of proteins are well known in the art. Random and/or combinatorial mutagenic approaches may alternatively or additionally be used for the creation of libraries of mutations, including approaches such as DNA shuffling, oligonucleotide cassette mutagenesis, error-prone PCR, molecular evolution and the use of mutator strains. A non-limiting list of mutagenic changes includes deletions, insertions, substitutions, rearrangements, point mutations and suppressor mutations. The products of the mutagenic methods should then be screened for the desired activity. Thus in some embodiments the enzyme of the invention is derived from an enzyme. By "derived" is meant that the enzyme contains one or more amino acid changes compared to the sequence of the wild-type enzyme, wherein the one or more changes includes deletions, insertions, substitutions, rearrangements, point mutations. The skilled person would understand that the EC classification system discussed in relation to the enzymes as described above is highly specific, and depends on the specific substrates catalysed by an enzyme. Accordingly, an enzyme of the invention derived from one of the enzymes may be classified in a different EC category to wild-type enzyme.

The enzymes used in the present methods may be improved with respect to a number of parameters. The enzyme may be improved over the wild-type enzyme with regard to the rate of reaction, so that the enzyme is able to convert more substrate to product in a defined period of time. This is advantageous because it decreases the time taken to perform the method of the invention. In an alternative, the enzyme may be improved over the wild-type enzyme with regard to the solvent stability of the enzyme in the presence of organic solvents. This is advantageous because in some embodiments, the method of the invention may be performed, in whole or in part, in a biphasic system, or a mixed solvent system (for example a mixed water/isopropanol system). In a further alternative, enzyme may be improved over the wild-type enzyme with regard to its activity at elevated temperatures. This is advantageous because it means that the method may be performed, in whole or in part, at temperatures which increase the rate of reaction (but which would have inactivated the wild-type enzyme). In a further alternative, the enzyme is engineered to reduce product inhibition and or substrate inhibition. This advantageously permits higher concentrations of the product and or substrate to be present in the reaction. In a further alternative the substrate reactivity of the enzyme may be altered. This means that the engineered enzyme is capable of reacting with a substrate that the wild-type enzyme cannot. Such enzymes are typically employed where a wild-type enzyme that is capable of performing the desired reaction is not known, or is not suitable. The substrate reactivity may also be changed by engineering the enzyme so that it is no longer able to accept and react with a substrate that the wild-type enzyme can.

1.2. Biocatalyst Formatting

The enzyme catalysts that are used in the methods of the invention may be introduced into the reaction in a variety of forms. In one alternative, each enzyme is in the same form. In another alternative, the enzymes are provided in different forms.

Whole cells that express one or more of the enzymes used in the methods of the invention may be used as the biocatalyst. The whole cells that are used typically possess a number of properties: they may be easily genetically modified, be tolerant of the conditions used in the method of the invention, and grow to cells densities which are industrially useful. Thus the invention provides a host cell comprising one or more of the enzymes detailed in above section or a non-naturally occurring variant thereof.

1.3. Modification of Whole Cell Biocatalysts

The biocatalysts used in the methods of the invention may be unmodified whole cells of the species in which the enzyme naturally occurs. Typically, however, it is necessary to modify genetically the host cell to produce an engineered cell. As used herein, an engineered cell means a cell that has been manipulated so that its genome has been altered from that of a wild-type cell. The alteration of the genome includes the introduction or deletion of genes of interest. In one alternative, the genetic modification is the introduction of a gene into the genome of the cell. The gene introduced into the cell may comprise a DNA sequence from another species or organism, for example a DNA sequence that is not present in the wild-type genome of the whole cell. In other instances, the introduced DNA sequence may be an extra copy of the gene in the genome of the whole cell. In some alternatives, the genetic modification is the deletion of a DNA sequence from the genome of the whole cell. In another alternative, the genetic modification is the modification of targeted genes by mutagenesis from the genome of the cell.

1.4. Metabolic Engineering of Whole Cells

Metabolic engineering has been defined as purposeful modification of intermediary metabolism of the cell/organism using recombinant DNA techniques. The whole cells used in the method of the present invention optionally have been engineered to optimise the output of the hexan-1,6-dioic acid, 1,6-hexamethylenediamine, caprolactam, 1,4-butanediol, 1,3-butanediol, 2,3-butanediol, 1,3-butadiene, or other compounds discussed above.

Metabolic engineering to increase the ability of a cell to produce a compound is principally performed via two avenues. The first is to optimise the enzymes in the pathway producing the desired product from the starting material. In a multi-enzyme pathway resulting in the production of hexan-1,6-dioic acid, 1,6-hexamethylenediamine, caprolactam, 1,4-butanediol, 1,3-butanediol, 2,3-butanediol, or 1,3-butadiene, other compounds discussed above, or a derivative thereof (as shown in the figures and described in the preceding sections), it is possible to determine the concentration of each intermediate in the pathway using techniques known to the skilled person (for example, two dimensional electrophoresis, the use of isotopically labelled precursors, mass spectrometry-based metabolomics, and nuclear magnetic resonance (NMR) spectroscopy), and therefore determine which of the enzyme conversions is the rate-limiting step. This can be determined by observing an accumulation of an intermediate, which indicates that the enzyme acting upon this intermediate is limiting the overall rate of conversion. In this instance, the rate at which this intermediate is reacted should therefore be increased. This can be performed by a number of means. Firstly, the expression level of the rate-limiting enzyme may be increased. Optionally this may be achieved by placing the gene encoding the enzyme under the control of a strong promoter, e.g., the T7 promoter if the enzyme is being expressed in *E. coli* or the TEF promoter if the enzyme is being expressed in yeast. The second option is to increase the number of copies of the gene encoding the enzyme that are present in cell, for instance by placing the gene in a multicopy plasmid, or by incorporating multiple copies of the gene into the chromosome of the host cell (these copies may be incorporated at the same location in the chromosome or in different locations in the chromosome). Thirdly, the enzyme may be subjected to mutagenesis to evolve the enzyme to react at a faster rate or to codon-optimize the enzyme to increase its expression. As noted above, one of the major limiting factors in the metabolism of glycerol is the uptake of glycerol by cells. Accordingly, one area of focus for the improvement of glycerol metabolism is expression and activity of the glycerol facilitator which actively transports glycerol into the host cell wherein the biocatalytic reactions turning glycerol into the useful nylon intermediates occur.

1.5. Growing Whole Cell Biocatalysts

In some embodiments of the invention whole cell biocatalysts are used which are growing (i.e. dividing) at the time the whole cells perform the conversions in the method of the invention. In these embodiments the cells are cultured under conditions which optimise the production of desired product (i.e. hexan-1,6-dioic acid, 1,6-hexamethylenediamine, caprolactam, 1,4-butanediol, 1,3-butanediol, 2,3-butanediol, or 1,3-butadiene, or other compounds discussed above and the like). As used herein, the term culture is equivalent with fermentation in a fermenter or bioreactor.

1.6. Compositions of the Invention

The invention also provides compositions comprising a host cell according to the invention and glycerol, hexan-1,6-dioic acid, 1,6-hexamethylenediamine, caprolactam, 1,4-butanediol, 1,3-butanediol, 2,3-butanediol, or 1,3-butadiene, or other compounds discussed above.

It is to be understood that the above-described compositions and modes of application are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

It is further to be understood that all values are approximate, and are provided for description.

Patents, patent applications, publications, product descriptions, and protocols cited throughout this application are incorporated herein by reference in their entireties for all purposes.

The invention claimed is:

1. A method for converting glycerol enzymatically to hexane-1,6-diamine, said method comprising culturing a genetically modified whole cell organism in the presence of glycerol, wherein
the genetically modified whole cell organism expresses an active glycerol transporter protein, an aldehyde dehydrogenase, and an aminotransferase or a diamine transaminase.

2. A recombinant host cell expressing an active glycerol transporter protein, an aldehyde dehydrogenase, and an aminotransferase or a diamine transaminase, wherein said host converts glycerol enzymatically to 6-aminohexanoic acid, and wherein said aldehyde dehydrogenase and said aminotransferase or said diamine transaminase convert 6-aminohexanoic to hexane-1,6-diamine.

3. A recombinant host cell according to claim 2, wherein said active glycerol transporter protein comprises
(i) a bacterial glycerol major intrinsic protein (MIP) channel;
(ii) a plant tonoplast intrinsic protein (TIP) or an algae aquaporin; or
(iii) a fungi or yeast glycerol channel protein.

4. A host cell according to claim 3, wherein the bacterial glycerol MIP channel is GipF.

5. A host cell according to claim 2, wherein the active glycerol transporter protein is a plant TIP.

6. A host cell according claim 2, wherein the active glycerol transporter protein is an algae aquaporin.

7. A host cell according to claim 2, wherein the fungi or yeast glycerol channel protein is Fps1.

8. The host cell according to claim 2, wherein the host cell comprises is *Yarrowia lipolytica*, *Candida* spp, *C. tropicalis*, *C. glycerinogenesis*, *C. albicans*, *C. cloacae*, *C. guillermondii*, *C. intermedia*, *C. maltosa*, *C. parapsilosis*, *C. zeylanoides*, an *Aspergillus* spp., a *Saccharomyces* spp., a *Rhodotorula* spp., a *Rhizopus* spp., a *Trichosporon* spp., a *Lipomyces* spp., a *Clostridium* spp., a *Pseudomonas* spp, or *Escherichia coli*.

9. The method of claim 1, wherein the glycerol has been produced as the by-product of bio-diesel production.

10. A recombinant host cell comprising an active glycerol transporter protein, an acetyl-CoA C-acetyltransferase (EC 2.3.1.9), a 3-hydroxybutyryl-CoA dehydrogenase (EC 1.1.1.157), and an oxidoreductase[EC 1.1.1.-], wherein the cell produces 1,3-butanediol from glycerol.

11. A recombinant host cell comprising an active glycerol transporter protein, an acetolactate synthase (EC 2.2.1.6), an acetolactate decarboxylase (EC 4.1.1.5), and a butanediol dehydrogenase (EC 1.1.1.4), wherein the cell produces 2,3-butanediol from glycerol.

12. The method of claim 1, wherein said active glycerol transporter protein is a bacterial glycerol major intrinsic protein (MIP) channel.

13. The method of claim 12, wherein said bacterial glycerol MIP channel is GipF.

* * * * *